US00PP35472P2

(12) United States Plant Patent
Couturieux

(10) Patent No.: US PP35,472 P2
(45) Date of Patent: Nov. 14, 2023

(54) ***HYDRANGEA* PLANT NAMED 'COUHAGIE'**

(50) Latin Name: ***Hydrangea* x *paniculata***
Varietal Denomination: COUHAGIE

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 18/115,289

(22) Filed: Feb. 28, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — Cassandra Bright

(57) ABSTRACT

A new and distinct cultivar of *Hydrangea* plant named 'COUHAGIE' is disclosed, characterized by large, conical-shaped panicles with flowers that age from cream to green. Plants have compact, v-shaped habits and brown stems. The new variety is a *Hydrangea*, typically produced as an outdoor ornamental plant.

2 Drawing Sheets

Latin name of the genus and species: *Hydrangea* x *paniculata.*

Variety denomination: 'COUHAGIE'.

BACKGROUND OF THE INVENTION

The new cultivar is a product of a planned breeding program conducted by the inventor in Vosges, France. The objective of the breeding program was to produce new *Hydrangea* varieties with compact plant habits and panicles with green sterile flowers. The crossing resulting in the new variety was made during 2010.

The seed and pollen parents cannot be identified as seed was bulk collected.

The new variety was found and selected by the inventor in 2012 at the same nursery in Vosges, France. Asexual reproduction of the new cultivar 'COUHAGIE' was first performed during 2012 in Vosges, France, by softwood cuttings. Through subsequent propagation, multiple additional generations have been reproduced, having shown that the unique features of this cultivar are stable and reproduced true to type.

SUMMARY OF THE INVENTION

The cultivar 'COUHAGIE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COUHAGIE.' These characteristics in combination distinguish 'COUHAGIE' as a new and distinct *Hydrangea* cultivar:

1. Large, conical shaped panicles.
2. Flowers age from cream to green.
3. Brown stem color.
4. Compact, v-shaped plant.

PARENT COMPARISON

Comparison cannot be made to the parent varieties are they cannot be identified.

COMMERCIAL COMPARISON

Plants of the new cultivar *Hydrangea* 'COUHAGIE' can be compared to the commercial variety *Hydrangea* 'Mont Blanc', unpatented. Plants of 'COUHAGIE' are similar to plants of 'Mont Blanc' in most horticultural characteristics, however, plants of 'COUHAGIE' differ in the following:

1. Plants of the new variety are more vigorous than plants of this comparator.

Plants of the new cultivar *Hydrangea* 'COUHAGIE' can be compared to the commercial variety *Hydrangea* 'Phantom', unpatented. Plants of 'COUHAGIE' are similar to plants of 'Phantom' in most horticultural characteristics, however, plants of 'COUHAGIE' differ in the following:

1. Flowers of the new variety are cream colored, turning green with maturity; flowers of this comparator are pure white.

Plants of the new cultivar *Hydrangea* 'COUHAGIE' can be compared to the commercial variety *Hydrangea* 'Silver Dollar', unpatented. Plants of 'COUHAGIE' are similar to plants of 'Silver Dollar' in most horticultural characteristics, however, plants of 'COUHAGIE' differ in the following:

1. Flowers of the new variety are cream colored, turning green with maturity; flowers of this comparator are pure white, turning soft pink.

BRIEF DESCRIPTION OF THE PHOTOGRAPHS

The accompanying photographs illustrate typical plants of 'COUHAGIE' grown outdoors in Vosges, France. Plants are approximately 2-3 years old, grown in the ground in a trial field. The Figures illustrate inflorescences of the new variety at different stages of maturity. The photographs were taken using conventional techniques and although colors may appear different from actual colors due to light reflectance it is as accurate as possible by conventional photographic techniques.

DETAILED BOTANICAL DESCRIPTION

Figure 1:
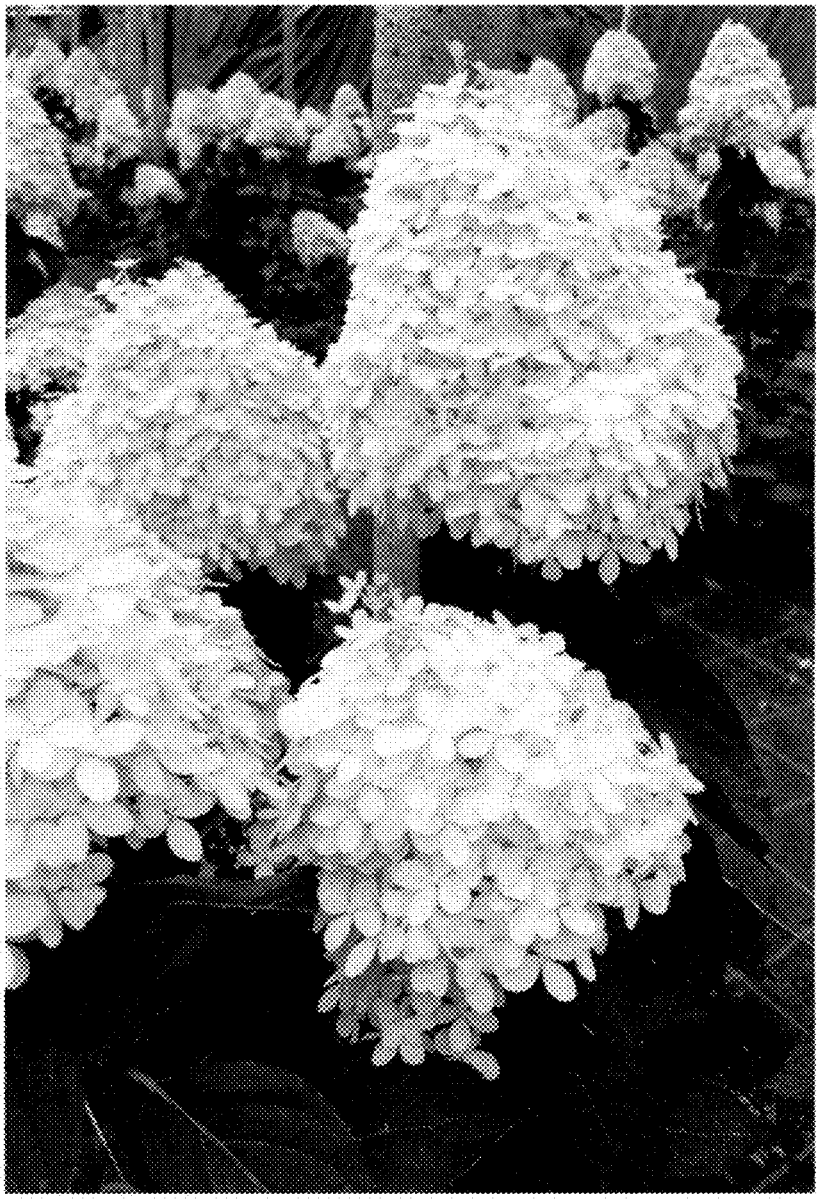
FIG. 1 illustrates a plant of 'COUHAGIE' with inflorescences just fully open, in bright light.
Figure 2:
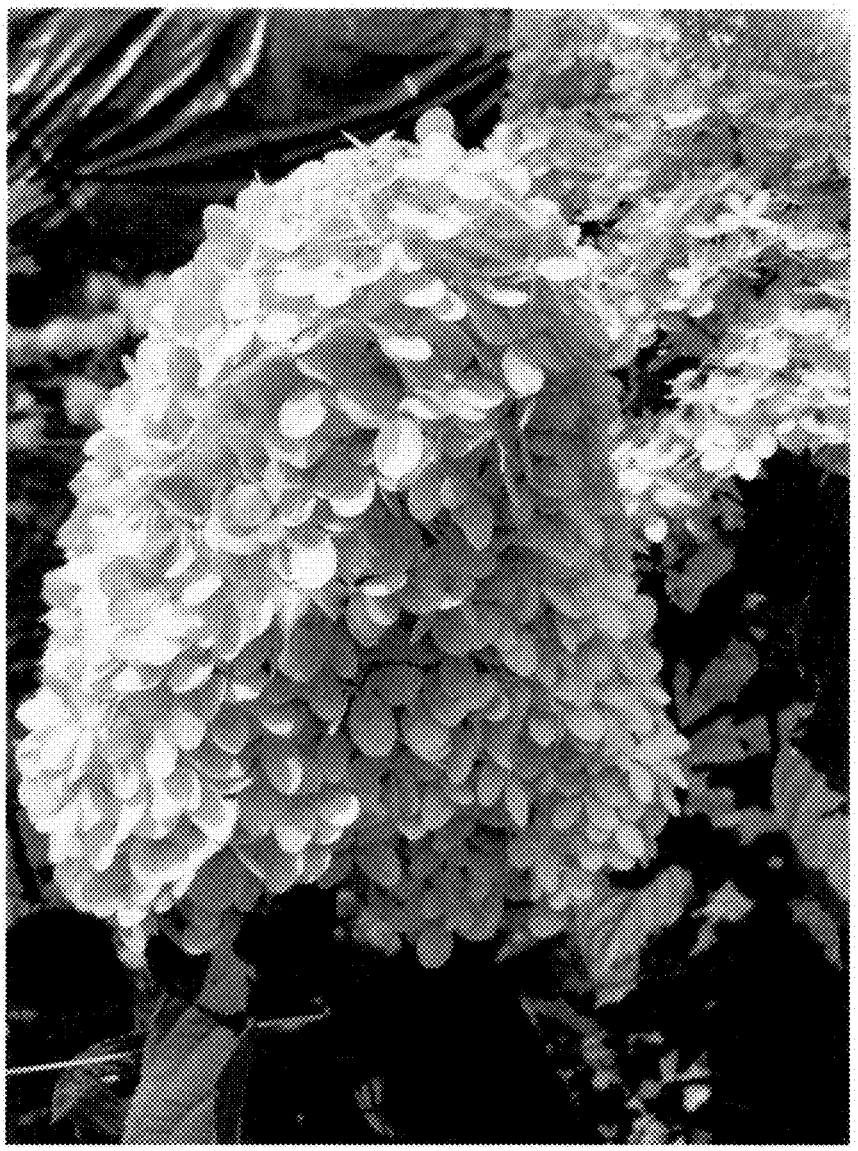
FIG. 2 illustrates a plant of 'COUHAGIE' with inflorescences in the fully mature stage of maturity.

In the following description, color references are made to The Royal Horticultural Society Colour Chart 2007, except where general terms of ordinary dictionary significance are used. The following observations and measurements describe 'COUHAGIE' plants grown in a ploy-greenhouse in Vosges, France. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea* x *paniculata* 'COUHAGIE'.

PROPAGATION

Typical method: Softwood cuttings.
Root initiation: 20 days at 20° C. during summer.
Time to produce rooted cutting: About 2 months at 20° C. during summer.
Roots: Dense, freely branching, fibrous, thick to thin. Creamy white to brown in color, not accurately measured with RHS chart.

PLANT

Growth habit: Upright, v-shaped, compact.
Height: 90 to 100 cm.
Plant spread: 70 cm.
Pot size of plant described: 2 gallon container.
Age of plant described: Approximately 2 years.
Growth rate: Good.
Plant vigor: Moderately vigorous.
Stem:
- *Branching.*—Basal.
- *Number of lateral branches.*—10.
- *Shape.*—Rounded.
- *Color.*—Immature: RHS Greyed-Purple N186 C. Mature: RHS Brown 200B with Grey-Brown 199A lenticels.
- *Length.*—80 cm.
- *Width.*—7 mm.
- *Aspect.*—70 to 80°.
- *Strength.*—Strong with some flexibility.
- *Pubescence.*—None.
- *Internode length.*—7 cm to 11 cm.

FOLIAGE

Leaf:
- *Arrangement.*—Whorl (3 leaves equally spaced around each node).
- *Shape.*—Broad elliptic to somewhat rounded deltate.
- *Length.*—10 to 12 cm.
- *Width.*—6 to 7.5 cm.
- *Apex.*—Acute.
- *Base.*—Obtuse.
- *Margin.*—Serrulate.
- *Texture of top surface.*—Roughly textured with coarse, bristly hairs.
- *Texture of bottom surface.*—Roughly textured with coarse, bristly hairs and pronounced venation.
- *Pubescence.*—Yes, upper and lower surfaces.
- *Color.*—Young foliage upper side: RHS Green 141A. Young foliage under side: RHS Green 141B. Mature foliage upper side: RHS Green 139A. Mature foliage, under side: RHS Green 137A.

Venation:
- *Type.*—Pinnate.
- *Color.*—Upper side: RHS Green 143C. Under side: Green 143D.

Petiole:
- *Length.*—5 cm.
- *Width.*—4 mm.
- *Color.*—RHS Green 143D.
- *Texture.*—Lightly pubescent.

INFLORESCENCE

Natural flowering season: Summer.
Inflorescence type: Mophead.
Panicle:
- *Shape.*—Conical.
- *Height.*—20 to 28 cm.
- *Diameter.*—15 to 22 cm.

Fragrance: Faintly sweet.
Sterile flowers:
- *Flowers per inflorescence.*—350 to 450.
- *Aspect.*—Outward.
- *Shape.*—Cruciform/stellate.
- *Length.*—3.5 cm.
- *Diameter.*—2.9 cm.
- *Persistent or self-cleaning.*—Persistent.

Bud:
- *Length.*—3 mm.
- *Diameter.*—3 mm.
- *Shape.*—Obovate.
- *Color.*—RHS Yellow-Green 150C.

Petals:
- *Number per flower.*—3 to 4.
- *Shape.*—Elliptic.
- *Tip.*—Acute.
- *Base.*—Truncate.
- *Margin.*—Entire.
- *Length.*—3 mm.
- *Width.*—2 mm.
- *Texture.*—Upper side: Smooth. Under side: Smooth.
- *Color.*—When Opening, Upper side: RHS Yellow-Green 150A. When Opening, Under side: RHS Yellow-Green 150A. Fully Opened, Upper side: RHS Green-White 157A flushed Green 143A. Fully Opened, Under side: RHS Green-White 157A flushed Green 143A.

Sepal:
- *Number per flower.*—4.
- *Shape.*—Ovate.
- *Tip.*—Broad rounded.
- *Base.*—Truncate.
- *Margin.*—Entire.
- *Length.*—1.9 cm.
- *Width.*—11 mm.

*Texture.*—Upper side: Smooth. Under side: Smooth.
*Color.*—Earliest Stage, Upper side: RHS Yellow-Green 150C. Earliest Stage, Under side: RHS Yellow-Green 150C. Semi-mature, Upper side: RHS Yellow-Green 150D. Semi-mature, Under side: RHS Yellow-Green 150D. Mature, Upper side: RHS Green-White 157B tinged Yellow-Green 150C. Mature, Under side: RHS Green-White 157B tinged Yellow-Green 150C.

Pedicel:
*Length.*—1 cm.
*Diameter.*—2 mm.
*Angle.*—45°.
*Strength.*—Good, flexible.
*Texture.*—Lightly pubescent.
*Color.*—RHS Yellow-Green 150C.

Fertile flowers: Absent or highly reduced and inconspicuous.

REPRODUCTIVE ORGANS

Sterile flower:
Stamens:
*Number.*—About 8.
*Filament color.*—RHS Yellow-Green 150C.
*Filament length.*—2 mm.

Anthers:
*Length.*—1 mm.
*Shape.*—Rounded.
*Color.*—RHS Yellow-Green 150C.
*Pollen.*—Scant.
*Pollen color.*—RHS Yellow-White 158C.

Pistil:
*Number.*—1.
*Length.*—1 mm.

Stigma:
*Shape.*—Bi-lobed.
*Color.*—RHS White 155A.
*Style length.*—0.5 mm.
*Style color.*—RHS White 155A.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −31° C. and tolerates an upper temperature range to at least 38° C.

Fruit/seed production: Not observed to date.

What is claimed is:

1. A new and distinct cultivar of *Hydrangea* plant named 'COUHAGIE' as herein llustrated and described.

* * * * *